United States Patent
Kawajiri et al.

(10) Patent No.: US 9,732,025 B2
(45) Date of Patent: Aug. 15, 2017

(54) PROCESS FOR EQUILIBRIUM-LIMITED REACTIONS

(71) Applicants: Dow Global Technologies LLC, Midland, MI (US); Georgia Tech Research Corporation, Atlanta, GA (US)

(72) Inventors: Yoshiaki Kawajiri, Atlanta, GA (US); Andreas Sebastian Bommarius, Atlanta, GA (US); Timothy C. Frank, Midland, MI (US); Megan E. Donaldson, Midland, MI (US); Jungmin Oh, Atlanta, GA (US); Gaurav Agrawal, Atlanta, GA (US)

(73) Assignees: Dow Global Technologies LLC, Midland, MI (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/888,535

(22) PCT Filed: May 2, 2014

(86) PCT No.: PCT/US2014/036605
§ 371 (c)(1),
(2) Date: Nov. 2, 2015

(87) PCT Pub. No.: WO2014/179709
PCT Pub. Date: Nov. 6, 2014

(65) Prior Publication Data
US 2016/0145184 A1    May 26, 2016

Related U.S. Application Data

(60) Provisional application No. 61/819,276, filed on May 3, 2013.

(51) Int. Cl.
| | | |
|---|---|---|
| *C07C 67/02* | (2006.01) | |
| *C07C 51/48* | (2006.01) | |
| *B01D 15/36* | (2006.01) | |
| *C07C 67/08* | (2006.01) | |
| *B01D 15/38* | (2006.01) | |
| *C07C 67/56* | (2006.01) | |
| *B01D 15/18* | (2006.01) | |

(52) U.S. Cl.
CPC ............ *C07C 51/48* (2013.01); *B01D 15/362* (2013.01); *B01D 15/3857* (2013.01); *C07C 67/08* (2013.01); *C07C 67/56* (2013.01); *B01D 15/1857* (2013.01); *Y02P 20/127* (2015.11)

(58) Field of Classification Search
None
See application file for complete search history.

(56) References Cited

U.S. PATENT DOCUMENTS

| 5,405,992 A | 4/1995 | Funk et al. |
| 6,444,842 B1 | 9/2002 | Gerberich et al. |
| 6,518,454 B1 | 2/2003 | Arumugam et al. |
| 6,586,609 B2 | 7/2003 | Ruggieri et al. |
| 7,667,068 B2 | 2/2010 | Miller et al. |

FOREIGN PATENT DOCUMENTS

CN    1515537    7/2004

OTHER PUBLICATIONS

F. Lode, et al., "Continuous Reactive Chromatography" Chemical Engineering Science, 56 (2001) 269-291 (24 pgs).
D. Gelosa, et al., "Chromatographic Reactors: Esterification of Glycerol with Acetic Acid Using Acidic Polymeric Resins", Industrial & Engineering Chemistry Research, vol. 42 (2003) 6536-6544 (10 pgs).
Gaurav Agrawal, et al., "Opimization of Reactive Simulated Moving Bed Systems with Modulation of Feed Concentration for Production of Glycol Ether Ester" Journal of Chromatography, vol. 1360 (2014).
International Search Report & Written Opinion for related PCT Application PCT/US2014/036605, mailed Nov. 19, 2014 (60 pgs).
International Preliminary Report on Patentability for related PCT Application PCT/US2014/036605, mailed Apr. 22, 2015 (8 pgs).

*Primary Examiner* — Yong Chu
*Assistant Examiner* — Ana Z Muresan
(74) *Attorney, Agent, or Firm* — Brooks, Cameron & Huebsch, PLLC

(57) ABSTRACT

A process for conducting equilibrium-limited chemical reactions that produce water as a reaction product. Specifically, a process that uses a reactive chromatography unit (RCU) to improve the efficiency of equilibrium-limited reactions, such as a process for reacting glycol ether (GE) and carboxylic acid (CA) to form water and glycol ether ester (GEE). The process includes supplying GE and CA to the RCU, where one of either the CA or the GE is in a stoichiometric deficit relative to the other reactant. The reactant in the stoichiometric deficit reacts in the presence of the catalyst in the RCU to form a mixture of GEE and water. A raffinate is separated from the mixture using the separation media of the RCU contains at least the GEE. An extract separated from the mixture using the separation media of the RCU contains at least the water.

12 Claims, 1 Drawing Sheet

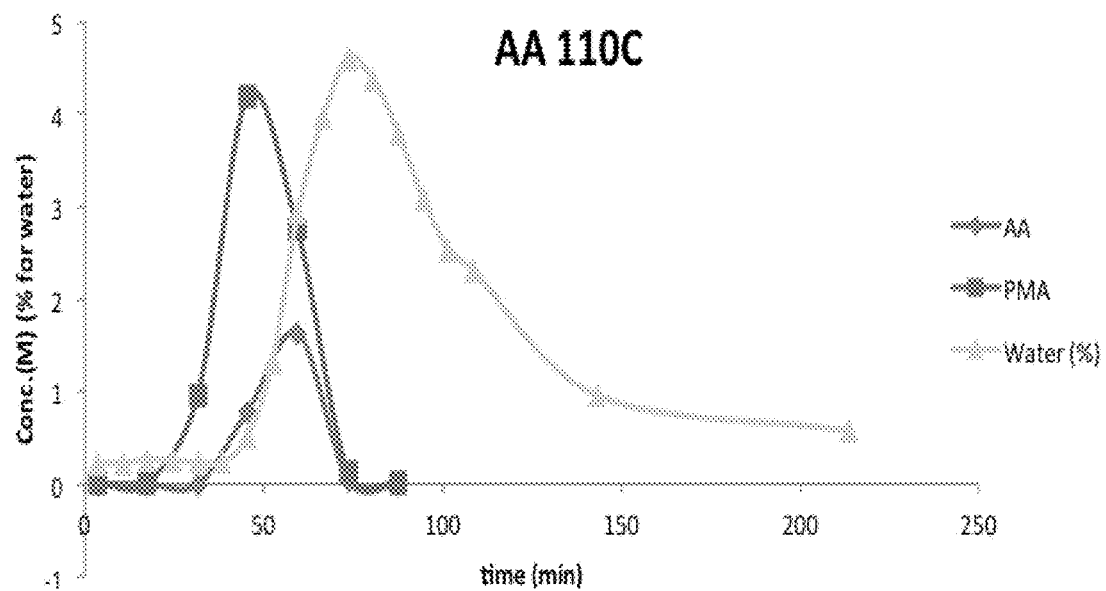

PROCESS FOR EQUILIBRIUM-LIMITED REACTIONS

This application is a National Stage Application under 35 U.S.C. §371 of International Application Number PCT/US2014/036605, filed May 2, 2014 and published as WO 2014/179709 on Nov. 6, 2014, which claims the benefit to U.S. Provisional Application 61/819,276, filed May 3, 2013, the entire contents of which are incorporated herein by reference in its entirety.

FIELD OF THE DISCLOSURE

The present disclosure relates generally to a process for equilibrium-limited reactions that produce water as a reaction product.

BACKGROUND

Esterification is a reaction in which an alcohol and an acid form an ester as a reaction product. Specifically, during an esterification reaction the alcohol and the acid react to form the ester and water. One process for conducting an esterification reaction is reactive distillation. Reactive distillation, which achieves separation of the desired product while carrying out the reaction in the same unit, is used in many applications. However, such methods rely on boiling point differences, and may not be applicable for thermally sensitive compounds. As such, there is a need in the art for an esterification reaction process that is useful for the reaction and subsequent separation of thermally sensitive compounds.

SUMMARY

The present disclosure provides for a process for conducting a variety of equilibrium-limited chemical reactions that produce water as a reaction product. Specifically, the present disclosure provides for a process of an equilibrium-limited reaction that uses a reactive chromatography unit (RCU) to improve the efficiency of equilibrium-limited reactions, where the equilibrium-limited reaction is a reversible reaction having an equilibrium conversion value ($X_e$) for a predetermined temperature. An example of such a process of an equilibrium-limited reaction of is reacting glycol ether (GE) and carboxylic acid (CA) at the predetermined temperature to form water and glycol ether ester (GEE). The process includes supplying GE and CA to the RCU, where one of either the CA is in a stoichiometric deficit relative to GE or the GE is in a stoichiometric deficit relative to CA. The RCU has a catalyst for the reaction at the predetermined temperature and media to separate a mixture that includes GEE and water. As discussed herein, separating this mixture produces a conversion value for the equilibrium limited reaction that is greater than the equilibrium conversion value for the predetermined temperature. So, the present disclosure helps to achieve a conversion that is greater than the equilibrium conversion value by separating and removing the reaction products, thereby driving the conversion of the reactants.

For example, when the CA is in the stoichiometric deficit relative to GE, the CA reacts in the presence of the catalyst in the RCU to form a mixture that includes GEE, GE, residual unreacted CA and water (e.g., via an esterification reaction). When the GE is in the stoichiometric deficit relative to CA, the GE reacts in the presence of the catalyst in the RCU to form a mixture that includes GEE, CA, residual unreacted GE and water (e.g., via an esterification reaction). A raffinate is separated from the mixture using the separation media of the RCU, where the raffinate contains at least the GEE. An extract is also separated from the mixture using the separation media of the RCU, where the extract contains at least the water.

When the CA is in the stoichiometric deficit relative to GE, the GE acts as an eluent for both the raffinate and the extract of the RCU. Additionally, residual unreacted CA may elute from the RCU in either the extract or the raffinate stream. It is preferable to operate the RCU in such a manner as to separate the residual unreacted CA into the extract stream to ease the downstream separation. So, the raffinate includes both the GEE and the GE, and the extract includes the water, residual unreacted CA, and the GE. The raffinate is separated from the mixture into a GEE fraction and a recycle fraction, where the recycle fraction contains the GE and a cut of the GEE. The recycle fraction is returned to the RCU to allow the GE to react with the CA. The extract can also be separated from the mixture into at least a GE/residual unreacted CA fraction (that contains both GE and residual unreacted CA) and a GE/Water fraction. The GE/residual unreacted CA fraction can be returned to the RCU to allow the GE and the residual unreacted CA to be recycled.

When the GE is in the stoichiometric deficit relative to CA, the CA acts as an eluent for both the raffinate and the extract of the RCU. Additionally, residual unreacted GE may elute from the RCU in either the extract or the raffinate stream. It is preferable to operate the RCU in such a manner, as discussed herein as to separate the residual unreacted GE into the extract stream to ease the downstream separation. So, the raffinate includes both the GEE and the CA, and the extract includes the water, residual unreacted GE, and the CA. The raffinate is separated from the mixture into a GEE fraction and a recycle fraction, where the recycle fraction contains the CA and a cut of the GEE. The recycle fraction is returned to the RCU to allow the CA to react with the GE. The extract can also be separated from the mixture into at least a CA/residual unreacted GE fraction (that contains both CA and residual unreacted GE) and a CA/Water fraction. The CA/residual unreacted GE fraction can be returned to the RCU to allow the CA and the residual unreacted GE to be recycled.

The RCU can be operated in such a manner that a single pass conversion of the CA in the stoichiometric deficit or the GE in the stoichiometric deficit can be from 70 percent (%) to 99%. As this conversion is less than 100%, there will be residual unreacted CA or residual unreacted GE in the mixture. Upon separation, the extract includes either the residual unreacted CA or the residual unreacted GE. By returning the residual unreacted CA or the residual unreacted GE to the RCU a higher overall conversion of CA and GE can be achieved. Such an overall conversion for CA and GE can approach 100% overall conversion.

The process of any provided herein includes the situation where the RCU is a simulated-moving bed unit.

The process of any provided herein includes the situation where the reaction is an esterification reaction.

The embodiments of the present disclosure include reacting the CA in the stoichiometric deficit relative to the GE to extinction with the catalyst in the RCU, or reacting the GE in the stoichiometric deficit relative to the CA to extinction with the catalyst in the RCU. Among other configurations, the RCU is a simulated-moving bed unit. The embodiments of the present disclosure can be used for equilibrium-limited chemical reactions that produce water as a reaction product, such as aldol condensations, esterification reactions, anhydride formation, and amidation reactions.

BRIEF DESCRIPTION OF FIGURES

FIG. 1 illustrates glycol ether conversion during an esterification reaction (Ex. 1).

DETAILED DESCRIPTION

The present disclosure provides a process for conducting equilibrium-limited chemical reactions at a predetermined temperature that can avoid the issues encountered with reactive distillation based processes (e.g., use of high temperatures or presence of azeotrope for separating the reaction products). The process of the present disclosure uses reactive chromatography for both the equilibrium-limited chemical reaction and the separation of the products, which allows for reaction and separation temperatures that should not harm the reaction products while still allowing for the continuous separation and removal of the reaction products. The use of reactive chromatography should also serve to improve the efficiency of equilibrium-limited reactions discussed herein by improving reaction conversion beyond the equilibrium-limit, providing for improved yields and simplified downstream purification of the reaction products.

As used herein, an "equilibrium constant" is an value that expresses the relationship between products and reactants of a reversible reaction at equilibrium at a given temperature with respect to a specific unit.

As used herein, an "equilibrium conversion" is the highest conversion ($X_e$) that can be achieved in a reversible reaction at a given temperature (e.g., an isothermal reaction temperature) for a constant volume system.

The process of the present disclosure uses a reactive chromatography unit (RCU) for equilibrium-limited chemical reactions at a predetermined temperature of a glycol ether (GE) and carboxylic acid (CA) to form a mixture that includes water and glycol ether ester (GEE). The equilibrium-limited reaction is a reversible reaction having an equilibrium conversion value ($X_e$) for the predetermined temperature. As discussed herein, the RCU allows for the reaction of the GE and CA and the separation of the water and GEE products to drive the conversion of this equilibrium-limited reaction. As provided herein, separating the water and GEE products produces a conversion value for the equilibrium-limited reaction that is greater than the equilibrium conversion value for the predetermined temperature. So, the present disclosure helps to achieve a conversion that is greater than the equilibrium conversion value by separating and removing the reaction products, thereby driving the conversion of the reactants. In addition to the RCU, distillation processes are used in the process of the present disclosure for the recycle of the mobile phase and further purification of the reaction products (e.g., ester product). As a result, by combining the RCU with the distillation procedure, it enables the recovery of more purified product and the recycle of mobile phase in a more efficient way.

The process of the present disclosure includes supplying to the RCU the GE and the CA. The RCU has a catalyst for the reaction and separation media to separate the mixture that includes GEE and water products into one of two streams: a raffinate and an extract. The CA reacts with the GE in the RCU to form the mixture that includes GEE and water. The raffinate contains at least GEE, while the extract contains at least the water.

In one embodiment, supplying GE and CA to the RCU includes supplying CA in a stoichiometric deficit relative to GE to the RCU. The CA, in the stoichiometric deficit relative to GE, reacts in the presence of the catalyst in the RCU to form the mixture that includes GEE and water. As the CA is supplied to the RCU is in a stoichiometric deficit relative to the GE, the GE supplied to the RCU is in a stoichiometric excess relative to the CA. Due to this stoichiometric excess the GE in addition to being a reactant in the reaction also acts as the eluent (is the chromatography elution solvent) for the extract and the raffinate of the RCU. Likewise, because the CA supplied to the RCU is in the stoichiometric deficit relative to the GE, the CA in the RCU can achieve a conversion value for the equilibrium-limited reaction that is greater than the equilibrium conversion value for the predetermined temperature in the presence of the catalyst in the RCU to form the mixture that includes the GEE and the water via the equilibrium-limited chemical reaction. In one embodiment, the CA in the RCU can react to extinction is so desired.

In another embodiment, supplying GE and CA to the RCU includes supplying GE in a stoichiometric deficit relative to CA to the RCU. The GE, in the stoichiometric deficit relative to CA, reacts in the presence of the catalyst in the RCU to form the mixture that includes GEE and water. As the GE is supplied to the RCU is in a stoichiometric deficit relative to the CA, the CA supplied to the RCU is in a stoichiometric excess relative to the GE. Due to this stoichiometric excess the CA in addition to being a reactant in the reaction also acts as the eluent (is the chromatography elution solvent) for the extract and the raffinate of the RCU. Likewise, because the GE supplied to the RCU is in the stoichiometric deficit relative to the CA, the GE in the RCU can achieve a conversion value for the equilibrium-limited reaction that is greater than the equilibrium conversion value for the predetermined temperature in the presence of the catalyst in the RCU to form the mixture that includes the GEE and the water via the equilibrium-limited chemical reaction. In one embodiment, the GE in the RCU can react to extinction is so desired.

The process of the present disclosure uses the RCU as both a reaction vessel and a chromatography unit. The RCU allows for the simultaneous reaction of reactants and separation of products for reversible reactions (e.g., an esterification reaction) to obtain enhanced performance. Examples of RCUs include one or more chromatographic columns packed with a catalyst for the esterification reaction and a separation media for the reaction products. Both the catalyst and the separation media can be present in the RCU as a stationary phase. The different reaction products can have different affinities to the stationary phase leading to different migration velocities through the RCU. This leads to the separation of the reaction products, suppression of backward reactions and providing high conversion at the outlet of the RCU.

One example of the RCU suitable for the present disclosure is a simulated-moving bed unit (SMB). The SMB unit provides for a continuous and counter-current operation that combines chemical reaction and separation within one single apparatus. The SMB unit employs multiple fixed-bed columns (or sections of columns), where each fixed bed column contains a catalyst for the acylation reaction and separation media to separate the water and the GEE reaction products. Different esterification reactions may require different number and configurations of the multiple fixed-bed columns. For example, from 4 to 24 fixed-bed columns can be used in forming an SMB unit for the esterification reactions of the present disclosure. The principal inputs and outputs of the SMB unit are the feed, the extract, and the raffinate, where each fixed-bed column includes an input stream and an output stream. Each stream flows into or out of the fixed-bed column of the SMB unit at individual locations and at a particular flow rate which is independently controlled.

During the process, the SMB unit switches input streams and the output streams of liquids from one column to another (or between column sections) to approach the theoretical performance of a true countercurrent solid-liquid flow. Switching the input streams and the output streams from one column to another can be accomplished using valves (e.g., rotary valves or a network of two-position or multi-position valves) which work in conjunction with the inlet and outlet lines of the multiple fixed-bed columns. The fluid-directing device accomplishes moving the locations of the input and output streams by directing the streams to the appropriate inlet or outlet lines of the multiple fixed-bed columns. The liquid flow rates of the feed streams and the step times for the valves of the SMB unit are controlled so that the slow and fast eluting reaction products move in opposite directions relative to the movement or switching of inlet and outlet ports.

The fixed-bed columns of the SMB unit are configured to provide four zones to provide for the esterification reaction and to separate the reaction products from the mixture into two fractions: the extract, which includes the slow-eluting fraction, and the raffinate, which includes the fast-eluting fraction. The four zones of the SMB unit each perform a different function. Zone I contains fixed-bed columns between the eluent inlet (e.g., the GE or the CA) and the extract outlet; Zone II contains fixed-bed columns between the extract outlet and the feed inlet (e.g., the CA or the GE or the mixture); Zone III contains fixed-bed columns between the feed inlet (e.g., the CA or the GE) and the raffinate outlet; and Zone IV contains fixed-bed columns between the raffinate outlet and the eluent inlet (e.g., the GE or the CA). Within the SMB unit, Zones II and III serve to allow the fast and slow components to move farther apart, while Zones I and IV serve to prevent the slow components from falling too far back and the fast components from moving too far forward, respectively.

As discussed herein, the fixed-bed columns of the SMB unit have a catalyst for the esterification reaction and separation media to separate the water and the GEE. The catalyst and the separation media can be provided on one structure or can be provided on separate structures in the fixed-bed columns of the SMB unit. The separation media used in the fixed-bed columns of the RCU can be selected so that the reaction components (e.g., the GE and the CA) are less strongly adsorbed, while the reaction co-products (e.g., the water) is more strongly adsorbed, thereby carrying them countercurrently with the simulated movement of the solids. This allows for less polar reaction component, e.g. the GEE, to be removed from the SMB unit in the raffinate stream, while more polar reaction component, e.g., the water, to be removed from the SMB unit in the extract stream.

The process of the present disclosure is for equilibrium-limited chemical reactions at a predetermined temperature that produce water, and not for equilibrium-limited chemical reactions that produce only non-aqueous reaction products (e.g., an alcohol). Examples of such reactions include, but are not limited to, aldol condensations, esterification reactions, anhydride formation, and amidation reactions. Examples of catalysts for aldol condensation reactions include, but are not limited to, to acidic, enzymatic or metal catalysts, as are known. Examples of catalysts for esterification reactions include, but are not limited to, to acidic polymeric resins, zeolites, heteropolyacids, and homogeneous catalysts, such as sulfuric acid [see, for example, G. Busca, "Acid Catalysts in Industrial Hydrocarbon Chemistry," Chem. Rev., 107 (11) (2007), 5366-5410]. Examples of catalysts for amidation reactions include, but are not limited to, to acidic or metal catalysts, as are known. Depending upon the composition of the feed, several different catalysts may be combined in order to accomplish the catalysis function.

The process of the present disclosure can use many different types of catalysts and separation media to carry out the reactions and separation. It can use either a single solid that can act as both catalyst and separation media, a combination of one or more solid catalysts and separation media, or a homogeneous catalyst with one or more separation media. The separation media can be conventional materials used in adsorption-type processes, including but are not limited to polymeric resins, silica, alumina, molecular sieves, activated carbon or other known separation media that can separate at least one of the products of the acylation reaction products. The preferred solids are those that can function as both catalyst and separation media in a single solid, such as strong acid ion exchange resins. These include but are not limited to a sulfonated ion exchange resin such as Amberlyst™ 15, Amberlyst™ 70, DOWEX™ MONOSPHERE™ M-31, or other commercially available strong acid polymeric resins.

Different reactions and separations of products may require different catalyst and separation media combinations and/or different volume ratios of catalyst to separation media. For example, the catalyst and the separation media can be present in the SMB unit in a volume ratio (catalyst:separation media) that ranges from 1:100 to 100:1. The catalyst and the separation media can also be present in the SMB unit in a variety of configurations. For example, when present as separate structures the catalyst and the separation media can be present as a homogeneous mixture throughout the fixed-bed columns of the SMB unit. Alternatively, the catalyst and the separation media can be present in alternating layers of catalyst and separation media along the fixed-bed columns of the SMB unit. The thicknesses and relative positions of the layers can depend upon the acylation reaction and the products that need to be separated.

For the process of the present disclosure, the GE and the CA are supplied to the RCU (e.g., the SMB unit), where the RCU has the catalyst for the reaction and separation media to separate the water and the GEE. The process operates continuously, with the GE and the CA being introduced, the reaction being catalyzed and the GEE and the water products being separated from the mixture into the raffinate and the extract, respectively.

As discussed herein, in one embodiment the CA is supplied to the RCU at a stoichiometric deficit relative to the GE, the GE acts as the eluent in both the raffinate and the extract, while the CA reacts in the RCU. In one embodiment, the CA in the stoichiometric deficit relative to the GE reacts is to extinction in the RCU.

Suitable examples of supplying the CA in the stoichiometric deficit relative to the GE for the reaction include supplying a stoichiometric ratio of CA to GE (CA:GE) in a range from 1:1.1 to 1:10; in a range from 1:1.5 to 1:5; or in a range from 1:2 to 1:3.

Also as discussed herein, in one embodiment the GE is supplied to the RCU at a stoichiometric deficit relative to the CA, the CA acts as the eluent in both the raffinate and the extract, while the GE reacts in the RCU. In one embodiment, the GE in the stoichiometric deficit relative to the CA reacts is to extinction in the RCU.

Suitable examples of supplying the GE in the stoichiometric deficit relative to the CA for the reaction include supplying a stoichiometric ratio of GE to CA (GE:CA) in a range from 1:1.1 to 1:10; in a range from 1:1.5 to 1:5; or in a range from 1:2 to 1:3. The feed introduced to the SMB unit contains at least one GE and at least one CA, where the SMB unit is operated at a pressure and a predetermined temperature suitable for the esterification reaction. Operating conditions will depend upon the catalyst and the separation media used in the SMB unit. Predetermined temperatures for the esterification reactions in the SMB unit can be from 0° C. to 200° C. Typical operating pressures for the esterification reactions in the SMB unit can be from 101 KPa to 2000 KPa. As appreciated by one skilled in the art, other predetermined temperatures and pressures are possible depending upon the esterification reaction. The operating conditions can be set so that the streams of the reactants (e.g., GE and CA) are in the liquid phase, and all components are in the liquid phase.

The GE can include, but are not limited to, those compounds that include a free hydroxyl group suitable for undergoing an esterification reaction. Specific examples of the GE include, but are not limited to, glycol ethers or combinations thereof. For example, the GE has the formula:

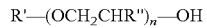

$$R'—(OCH_2CHR'')_n—OH$$

where R' is an alkyl group having 1 to 8 carbon atoms or an aryl group having 6 to 11 carbon atoms; R'' is hydrogen, methyl, or ethyl; and n is an integer from 1 to 4.

The CA can include, but are not limited to, those selected from the group consisting of formic acid, acetic acid, propionic acid, butyric acid, benzoic acid, adipic acid or a combination thereof. In one embodiment, the CA is acetic acid, while the GE is 1-methoxy-2-propanol. In other embodiments, the process of the present disclosure can be used in aldol condensations, esterification reactions, anhydride formation, and amidation reactions.

As discussed herein, the separation media of the RCU allow for separating from the mixture the raffinate and the extract. The raffinate contains at least the GEE, while the extract contains at least the water. In the embodiment where the GE is used as the eluent, the raffinate and the extract also contains GE (e.g., the raffinate includes GEE and GE, and the extract includes water and GE, where the raffinate is less polar relevant the extract). Alternatively, where the CA is used as the eluent, the raffinate and the extract also contains CA (e.g., the raffinate includes GEE and CA, and the extract includes water and CA, where the raffinate is less polar relevant the extract). Additionally, residual unreacted GE or CA (depending on the limiting reagent) may elute from the RCU in either the extract or the raffinate stream. It is preferable to operate the RCU in such a manner as to separate the residual unreacted GE or CA into the extract stream to ease the downstream separation. For example, the flow rates in each zone of the SMB (related to both residence time for reaction and separation), the throughput, concentration, temperature can each be modified to achieve proper separation of the correct species into the desired streams. It is also possible that undesirable heavy compounds can be present in either of the product streams, where the heavy compounds were present in the feed or were produced as undesired by-products of the reaction (e.g., the esterification reaction).

The raffinate can undergo a separation process to separate the raffinate from the mixture into a GEE fraction and a recycle fraction. When the GE is used as the eluent the recycle fraction contains the GE and a cut of the GEE. The recycle fraction can be returned to the RCU (e.g., the SMB unit), while the GEE fraction is collected as a product. Any heavy compounds can be removed as bottoms from the separation. The recycle fraction can be returned to the feed of the RCU. In an additional embodiment, the recycle fraction can be returned to a location within the RCU where the molar compositions of the GE and the GEE in the recycle fraction have similar values to the molar concentrations of the GE and the GEE in the RCU (e.g., a point of similar concentration in the chromatography cycle of the SMB unit).

In the embodiment in which the CA is the eluent, the recycle fraction contains the CA and a cut of the GEE. The recycle fraction can be returned to the RCU (e.g., the SMB unit), while the GEE fraction is collected as a product. Any heavy compounds can be removed as bottoms from the separation. The recycle fraction can be returned to the feed of the RCU. In an additional embodiment, the recycle fraction can be returned to a location within the RCU where the molar compositions of the CA and the GEE in the recycle fraction have similar values to the molar concentrations of the CA and the GEE in the RCU (e.g., a point of similar concentration in the chromatography cycle of the SMB unit).

Suitable separation process for the raffinate include, but are not limited to, distillation processes, as are known, that can form the GEE fraction and a recycle fraction. Examples of suitable distillation process include continuous distillation processes, including those that use a dividing wall column (DWC). Other separation processes are also possible.

The extract also undergoes a separation process. For example, when the GE is used as the eluent the extract undergoes a separation process to separate from the mixture the extract into at least a GE/residual unreacted CA fraction and a GE/Water fraction. The GE/residual unreacted CA fraction contains both GE and residual unreacted CA (e.g., CA that did not react with the GE). The GE/residual unreacted CA fraction can be returned to the feed of the RCU (e.g., the SMB unit), while the GE/Water fraction is removed from the process.

In the other embodiment, when the CA is used as the eluent the extract undergoes a separation process to separate from the mixture the extract into at least a CA/residual unreacted GE fraction and a CA/Water fraction. The CA/residual unreacted GE fraction contains both GE and residual unreacted CA (e.g., CA that did not react with the GE). The CA/residual unreacted GE fraction can be returned to the feed of the RCU (e.g., the SMB unit), while the CA/Water fraction is removed from the process.

Suitable separation processes for the extract include, but are not limited to, those discussed herein for the raffinate. The GE/Water fraction and/or the CA/Water fraction may form an azeotropic mixture, which cannot be separated by ordinary distillation. Separating the GE/Water fraction or the CA/Water fraction may require homogeneous azeotropic distillation, pressure-swing distillation, or a heterogeneous azeotropic distillation processes in order to separate the GE and the water of the GE/Water fraction. Examples of such azeotropic distillation processes are discussed in Volume 8 of Kirk-Othmer Encyclopedia of Chemical Technology ($5^{th}$ Edition, John Wiley & Sons), incorporated herein by reference in its entirety. Alternative separation options include hot gas pressure swing adsorption with 3 Å molecular sieves.

As discussed herein, the CA can react above the equilibrium limited conversion with the GE or the GE can react above the equilibrium limited conversion with the CA. When the reactant in the stoichiometric deficit (e.g., the CA or the GE) does not all react in the RCU, it emerges from the RCU. As previously indicated, the unreacted reactant is preferably separated into the extract stream for easier downstream processing.

In a preferred embodiment, the RCU is operated in such a manner as to enable high overall conversion of the reactant in the stoichiometric deficit (e.g., the CA or the GE) without requiring a single high conversion (e.g., greater than 90% conversion of the reactant in the stoichiometric deficit (e.g., the CA or the GE)) through the RCU itself. By not attempting to achieve the highest possible single-pass conversion, but rather a single-pass conversion that is lower than the highest possible value, the overall consumption of the reactant in the stoichiometric excess acting as the elution solvent can be reduced. This can be accomplished through the strategy described herein in which the recycle fraction from the raffinate and the GE/residual unreacted CA fraction or the CA/residual unreacted GE fraction is returned to the RCU. In addition, the flow rates in each zone of the SMB (related to both residence time for reaction and separation), the throughput, concentration, temperature can each be modified to achieve a desired single-pass conversion that is lower than the highest possible value. The reactant in the stoichiometric excess acting as the elution solvent can be minimized while achieving high overall conversion by providing for economical recovery and recycle of the residual unreacted CA or residual unreacted GE. For example, the optimum single-pass conversion may range from 70 to 99% conversion of the CA in the stoichiometric deficit or the GE in the stoichiometric deficit to enable reduced eluent requirements while achieving high overall conversions approaching 100%.

The residual unreacted CA or residual unreacted GE can also be recovered as a third product from the RCU. In one embodiment, this third product from the RCU can be recovered from the RCU by employing a multi-component SMB separation scheme. Examples of such schemes for utilizing SMB units, as discussed herein, for separating tertiary reaction mixtures (e.g., raffinate, extract and unreacted CA) can be found in "Comparison of various ternary simulated moving bed separation schemes by multi-objective optimization" (Agrawal et al., Journal of Chromatography A, 1238 (2012) 105-113), which is incorporated herein by reference in its entirety.

As appreciated by one skilled in the art, the separation of the product mixture into the raffinate and the extract in the RCU might be enhanced by the use of a non-reactive solvent in addition to the GE or CA of the mobile phase. Examples of such non-reactive solvents can include, but are not limited to, a ketone. This use of an added mobile phase solvent would be optional, but could be useful to enhance the separation ability of the RCU for the present disclosure. In addition, the process for reacting the GE and the CA to form the mixture comprising water and the GEE by supplying to the RCU the GE and the CA can include the use of the non-reactive solvent as the mobile phase, where the GE and the CA are supplied in equal stoichiometric amounts.

EXAMPLES

The following example is given to illustrate, but not limit, the scope of this disclosure. Unless otherwise indicated, all parts and percentages are by weight. Unless otherwise specified, all instruments and chemicals used are commercially available.

Example 1 (Ex. 1)

Ex. 1 is the reversible esterification of 1-methoxy-2-propanol (Alfa Aesar, 99+%) with acetic acid (AA, BDH, >99%) using the following reactive chromatography test. Dry Amberlyst™ 15 (Sigma Aldrich, wet condition) at 66° C. and sieve to collect only the portion of size in less than 707 μm in diameter. Form a slurry with the dried Amberlyst™ 15 and 1-methoxy-2-propanol (Sigma Aldrich, ≥99.5%). Pack two stainless steel columns (Knauer, inner diameter 0.8 centimeters, length 0.25 meters) with the Amberlyst™ 15 slurry. Set up the columns in a series and provide a high pressure liquid chromatography (HPLC) pump in a basic HPLC configuration. Place the two columns into a column oven set at a temperature of 110° C. Use the HPLC pump to pump the 1-methoxy-2-propanol as the eluent through the columns at a rate of 0.5 milliliter/minute (mL/min). Using a back pressure valve achieve a pressure in the columns of 150 pounds per square inch gauge (psig). Between the outlet of the column and the fraction collector place an ice bath to cool the stream to below the boiling temperature at 1 atmosphere. Add the acetic acid to the columns through a manual valve (Rheodyne manual injector, RH-7725I), using an HPLC pump to directly add a 0.5 milliliter (ml) rectangular pulse onto the columns. Collect the effluent from the columns at a constant time interval and analyze by gas chromatography and Karl Fischer titration.

Comparative Example A (Comp. Ex. A)

Comp. Ex. A repeats the esterification reaction of Ex. 1, but done in a batch configuration. For the batch configuration, load 1.5 mL Eppendorf test tubes with 0.13 grams (g) of Amberlyst™ 15 resin, 0.7 mL of PM and 0.7 mL of acetic acid. Place tubes on a thermomixer where the temperature is controlled from 40° C. to 80° C. and the mixing rate was set at 800 rpm. Take samples periodically and analyze by GC-FID.

FIG. 1 illustrates that the separation of the reaction products for Ex. 1 was achieved. FIG. 1 also illustrates that for Ex. 1 the conversion of the acetic acid exceeded the equilibrium-limit in achieving a conversion of approximately 80 weight percent (wt. %) based on the reaction products (estimated from calculations using the trapezoidal rule) formed over 100 minutes. This is a significant improvement from the batch experiment of Comp. Ex. A, where Table 1 illustrates that only 68 wt. % (based on the reaction products) of acetic acid converted after 24 hours. This result is believed to be due to achieving reaction equilibrium for the esterification reaction.

TABLE 1

| No. | Temp (° C.) | Catalyst loading (g) ± 0.01 | PM Initial Vol. (mL) | PM Initial Conc. (M) | PM Final Conc. (M) | Acetic acid Initial Vol. (mL) | Acetic acid Initial Conc. (M) | Acetic acid Final Conc. (M) | PMA Final Conc. (M) | Est. Rxn time |
|---|---|---|---|---|---|---|---|---|---|---|
| 1 | 40 | 0.13 | 0.7 | 5.11 | 1.57 | 0.7 | 8.73 | 5.82 | 2.95 | 24 hr |
| 2 | 50 | 0.13 | 0.7 | 5.11 | 1.62 | 0.7 | 8.73 | 5.73 | 3.05 | 24 hr |
| 3 | 60 | 0.13 | 0.7 | 5.11 | 1.60 | 0.7 | 8.73 | 5.80 | 3.21 | 24 hr |
| 4 | 70 | 0.13 | 0.7 | 5.11 | 1.67 | 0.7 | 8.73 | 5.79 | 3.08 | 24 hr |
| 5 | 80 | 0.13 | 0.7 | 5.11 | 1.62 | 0.7 | 8.73 | 5.73 | 3.05 | 20 hr |

PMA—propylene glycol methyl ether acetate

As discussed herein, reactive chromatography is a process that combines reaction and separation in a single unit that leads to a greater process performance and productivity. This process is especially advantageous when the reaction is equilibrium-limited, and the in-situ separation of product shifts the equilibrium in the direction of conversion increase.

The application of reactive chromatography to the synthesis of an ester using Amberlyst 15 as a catalyst and adsorbent is provided for herein. Among numerous esters, the production of propylene glycol methyl ether acetate (DOWANOL™ PMA), one of the most commonly used esters with a high industrial demand, is possible. PMA is the second-most used propylene glycol ether with nearly 90% of its use in surface coatings. It is very efficient at dissolving resins used in paints, inks, lacquers, and other types of surface coatings such as in automotive, architectural, metal-coil, and industrial maintenance coatings. Also, it is used in household products such as cleaners, paints (including spray paint), lacquers, varnishes, and pesticides. However, no study has been conducted on reactive chromatography for the formation of PMA, either through the esterification of 1-methoxy-2-propanol (PM) with acetic acid or through the transesterification of PM with ethyl acetate.

The process development for a new ester product is provided for herein. The dynamics of batch reaction and the fixed-bed adsorptive reaction are investigated by carrying out batch reaction experiments and chromatographic pulse tests. Stirred batch reactor experiments were conducted at various temperatures, stirring speeds, catalyst particle size and loading, and mole ratio of reactants. Reaction equilibrium and kinetic parameters together with their dependence on temperature were determined by fitting the model to the experimental data. Measurement of the adsorption equilibrium constant and reaction parameters were conducted by the pulse tests using a single chromatographic column. Since the resin acts as both adsorbent and catalyst, experiments were performed with nonreactive mixtures to obtain adsorption parameters first, and then reactive mixtures were injected to obtain reaction parameters. In addition to the development of model, the feasibility and efficiency of reactive chromatography where the conversion exceeds the reaction equilibrium of the batch reaction were demonstrated.

We claim:

1. A process for an equilibrium-limited reaction of glycol ether (GE) and carboxylic acid (CA) to form a mixture comprising water and glycol ether ester (GEE), where the equilibrium-limited reaction is a reversible reaction having an equilibrium conversion value ($X_e$) for a predetermined temperature, the process comprising:
supplying to a reactive chromatography unit (RCU) GE and CA in a stoichiometric deficit relative to GE, where the RCU includes a sulfonated ion exchange resin that acts as both catalyst for the reaction and media to separate GEE and water and the GE acts as an eluent in both a raffinate and an extract;
reacting at the predetermined temperature CA and GE in the presence of the sulfonated ion exchange resin in the RCU to form the mixture comprising GEE and water; and
separating the product mixture with the sulfonated ion exchange resin into the raffinate and the extract, where separating the product mixture produces a conversion value for the equilibrium limited reaction that is greater than the equilibrium conversion value for the predetermined temperature.

2. The process of claim 1, where the raffinate includes GEE and GE and the process further comprises:
separating the raffinate from the mixture into a GEE fraction and a recycle fraction, where the recycle fraction contains the GE and a cut of the GEE; and
returning the recycle fraction to the RCU.

3. The process of claim 1, further comprising separating the extract from the mixture into at least a GE/residual unreacted CA fraction containing both GE and residual unreacted CA and an GE/Water fraction; and
returning the GE/residual unreacted CA fraction to the RCU.

4. The process of claim 1, where reacting CA in the stoichiometric deficit relative to GE is to extinction in the presence of the catalyst in the RCU.

5. The process of claim 1, where CA is selected from the group consisting of acetic acid, propionic acid, butyric acid or a combination thereof.

6. The process of claim 1, where the GE has the formula:

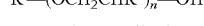
R'—(OCH$_2$CHR")$_n$—OH where R' is an alkyl group having 1 to 8 carbon atoms or an aryl group having 6 to 11 carbon atoms; R" is hydrogen, methyl, or ethyl; and n is an integer from 1 to 4.

7. A process for an equilibrium-limited reaction of glycol ether (GE) and carboxylic acid (CA) to form a mixture comprising water and glycol ether ester (GEE), where the equilibrium-limited reaction is a reversible reaction having an equilibrium conversion value ($X_e$) for a predetermined temperature, the process comprising:
supplying to a reactive chromatography unit (RCU) CA and GE in a stoichiometric deficit relative to CA, where the RCU includes a sulfonated ion exchange resin that acts as both catalyst for the reaction and media to separate GEE and water and the CA acts as an eluent in both a raffinate and an extract;
reacting at the predetermined temperature CA and GE in the presence of the sulfonated ion exchange resin in the RCU to form the mixture comprising GEE and water; and separating the product mixture with the sulfonated ion exchange resin into the raffinate and the extract, where separating the product mixture produces a conversion value for the equilibrium limited reaction that is greater than the equilibrium conversion value for the predetermined temperature.

8. The process of claim 7, where the raffinate includes GEE and CA; the process further comprising separating the raffinate from the mixture into a GEE fraction and a recycle fraction, where the recycle fraction contains the CA and a cut of the GEE; and returning the recycle fraction to the RCU.

9. The process of claim 7, including separating the extract from the mixture into at least a CA/residual unreacted GE fraction that contains both CA and residual unreacted GE and a CA/Water fraction; and returning the CA/residual unreacted GE fraction to the RCU.

10. The process of claim 7, where reacting GE in the stoichiometric deficit relative to CA is to an extinction of the GE with the catalyst in the RCU.

11. The process of claim 7, where CA is selected from the group consisting of acetic acid, propionic acid, butyric acid or a combination thereof.

12. The process of claim 7, where the GE has the formula:

$$R'-(OCH_2CHR'')_n-OH$$

where R' is an alkyl group having 1 to 8 carbon atoms or an aryl group having 6 to 11 carbon atoms; R" is hydrogen, methyl, or ethyl; and n is an integer from 1 to 4.

* * * * *